United States Patent
Efraty et al.

(10) Patent No.: US 10,366,483 B2
(45) Date of Patent: Jul. 30, 2019

(54) WAFER NOTCH DETECTION

(71) Applicant: KLA-TENCOR CORPORATION, Milpitas, CA (US)

(72) Inventors: Boris Efraty, Carmiel (IL); Nassim Bishara, Cupertino, CA (US); Arkady Simkin, Yokneam Ilit (IL); Yaron Ish-Shalom, Kyryat Tivon (IL)

(73) Assignee: KLA-Tencor Corporation, Milpitas, CA (US)

( * ) Notice: Subject to any disclaimer, the term of this patent is extended or adjusted under 35 U.S.C. 154(b) by 485 days.

(21) Appl. No.: 14/958,535

(22) Filed: Dec. 3, 2015

(65) Prior Publication Data

US 2016/0086325 A1    Mar. 24, 2016

Related U.S. Application Data

(63) Continuation of application No. PCT/US2015/015270, filed on Feb. 10, 2015.
(Continued)

(51) Int. Cl.
*G06K 9/52* (2006.01)
*G06T 3/20* (2006.01)
(Continued)

(52) U.S. Cl.
CPC .......... *G06T 7/0004* (2013.01); *G01B 11/002* (2013.01); *G01N 21/8851* (2013.01);
(Continued)

(58) Field of Classification Search
CPC .......... G06T 7/0004; G06T 3/20; G06T 7/60; G06T 2207/20056; G06T 2207/30148;
(Continued)

(56) References Cited

U.S. PATENT DOCUMENTS 5,825,913 A   10/1998   Rostami et al.
6,440,821 B1   8/2002   Conboy et al.
(Continued)

FOREIGN PATENT DOCUMENTS

CN   102347224 A   2/2012
EP   0641021 B1   12/1999
(Continued)

OTHER PUBLICATIONS

Use of Wafer Backside Inspection and SPR to Address Systemic Tool and Process Issues; Alan Carlson, Prasad Bachiraju, Jennifer Clark, Dale Trost; Presented at SPIE—Feb. 2010.
(Continued)

*Primary Examiner* — Jared Walker
(74) *Attorney, Agent, or Firm* — Suiter Swantz pc llo

(57) ABSTRACT

Notch detection methods and modules are provided for efficiently estimating a position of a wafer notch. Capturing an image of specified region(s) of the wafer, a principle angle is identified in a transformation, converted into polar coordinates, of the captured image. Then the wafer axes are recovered from the identified principle angle as the dominant orientations of geometric primitives in the captured region. The captured region may be selected to include the center of the wafer and/or certain patterns that enhance the identification and recovering of the axes. Multiple images and/or regions may be used to optimize image quality and detection efficiency.

20 Claims, 6 Drawing Sheets

Related U.S. Application Data

(60) Provisional application No. 61/939,131, filed on Feb. 12, 2014.

(51) Int. Cl.
| | | |
|---|---|---|
| *G06T 7/60* | (2017.01) | |
| *G06T 7/00* | (2017.01) | |
| *H01L 21/68* | (2006.01) | |
| *G01B 11/00* | (2006.01) | |
| *G01N 21/88* | (2006.01) | |
| *G01N 21/95* | (2006.01) | |

(52) U.S. Cl.
CPC ........... *G01N 21/9501* (2013.01); *G06K 9/52* (2013.01); *G06T 3/20* (2013.01); *G06T 7/60* (2013.01); *H01L 21/681* (2013.01); *G06T 2207/20056* (2013.01); *G06T 2207/30148* (2013.01)

(58) Field of Classification Search
CPC .. G01N 21/8851; G01N 21/9501; G06K 9/52; G01B 11/002; H01L 21/681
USPC .......................................................... 348/94
See application file for complete search history.

(56) References Cited

U.S. PATENT DOCUMENTS

| | | |
|---|---|---|
| 6,559,457 B1 | 5/2003 | Phan et al. |
| 7,280,200 B2 | 10/2007 | Phemmons et al. |
| 7,684,611 B2 | 3/2010 | Simpkins |
| 2004/0151917 A1 | 8/2004 | Chen et al. |
| 2005/0013476 A1 | 1/2005 | Simpkins |
| 2007/0139642 A1 | 6/2007 | Ikeda et al. |
| 2009/0161097 A1* | 6/2009 | Friedrich ........... G01N 21/9501 356/237.5 |
| 2010/0075442 A1 | 3/2010 | Hayashi et al. |
| 2010/0207249 A1 | 8/2010 | Sugawara et al. |
| 2011/0141272 A1 | 6/2011 | Uto et al. |
| 2011/0260057 A1* | 10/2011 | Otaka ..................... H01J 37/20 250/307 |

FOREIGN PATENT DOCUMENTS

| | | |
|---|---|---|
| EP | 1176628 A2 | 1/2002 |
| EP | 1437762 A1 | 7/2004 |
| JP | 2000031245 A | 1/2000 |
| JP | 2002280287 A | 9/2002 |
| JP | 2011238649 A | 11/2011 |
| WO | 2005077135 A2 | 8/2005 |

OTHER PUBLICATIONS

Precise [100] crystal orientation determination on (110)-oriented silicon wafers; Fan-Gang Tseng et al.; Institute of Physics Publishing; Journal of MicroMechanics and Microengineering; Engineering and System Science Department, National Tsing Hua University, Hsinchu, Taiwan, Republic of China; in final form Sep. 27, 2002; Published Nov. 7, 2002; Online at stacks.iop.org/JMM/13/47.
High throughput wafer defect monitor for integrated metrology applications in photolithography; Nagaraja Rao et al.; Real Time Metrology, Inc.; Metrology, Inspection, and Process Control for Microlithography, XXII, edited by John A. Allgair, Christopher J. Raymond; Proc. of SPIE vol. 6922, 69223B, (2008), 0277-786X/08/$18, doi: 10.1117/12.772384.
TW Office Action dated Jun. 11, 2018 for Taiwan Patent Application No. 104104793.
Office Action dated Oct. 29, 2018 for Chinese Patent Application No. 201580008392.9.

* cited by examiner

200

210 — ESTIMATING A POSITION OF A WAFER NOTCH

220 — CAPTURING AN IMAGE OF A SPECIFIED SECTION OF THE WAFER

222 — CAPTURING AN IMAGE OF A CENTRAL SECTION OF THE WAFER

225 — CAPTURING MULTIPLE IMAGES AND SELECTING IMAGES FOR FURTHER PROCESSING ACCORDING TO IMAGE CHARACTERISTICS

228 — FINDING THE DOMINANT ORIENTATION OF GEOMETRIC PRIMITIVES IN THE FIELD OF VIEW

230 — TRANSFORMING THE CAPTURED IMAGE

235 — CALCULATING FOURIER TRANSFORM COEFFICIENTS FOR THE CAPTURED IMAGE

240 — CONVERTING THE TRANSFORMED IMAGE INTO POLAR COORDINATES

Figure 5

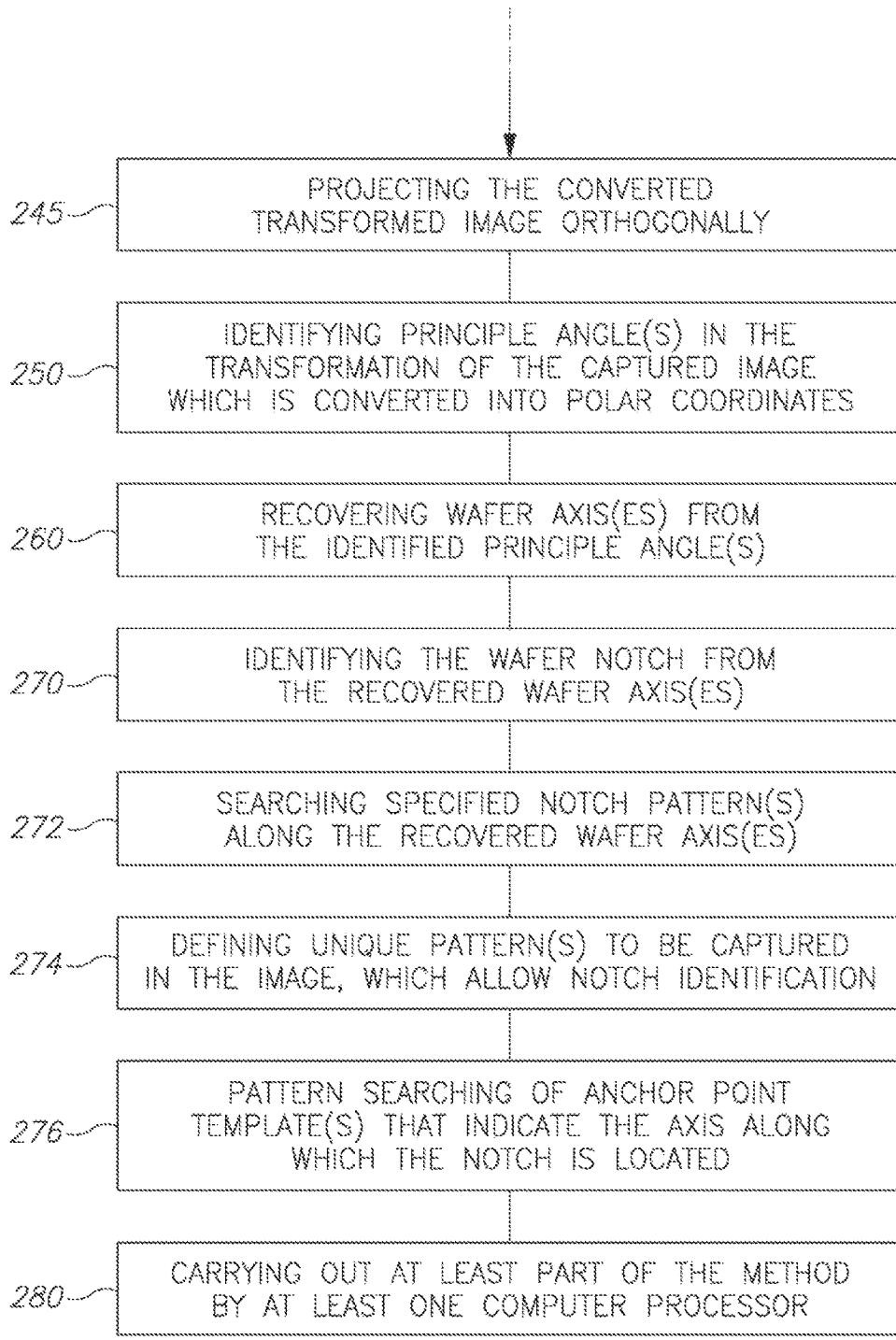
Figure 5 (cont. 1)

WAFER NOTCH DETECTION

CROSS REFERENCE TO RELATED APPLICATIONS

This application is filed under 35 U.S.C. § 120 and § 365(c) as a continuation of International Patent Application Serial No. PCT/US15/15270, filed on Feb. 10, 2015, which application claims the benefit under 35 U.S.C. 119(e) of U.S. Provisional Patent Application No. 61/939,131 filed on Feb. 12, 2014, which applications are incorporated herein by reference in their entirety.

FIELD OF THE INVENTION

The present invention relates to the field of semiconductor technology, and more particularly, to identification of the position of the wafer notch.

BACKGROUND OF THE INVENTION

Typically, the wafer orientation is conveyed by the position of the notch, which indicates the crystallographic orientation of wafer. In the prior art, wafer orientation computation based on notch orientation is time consuming, as it requires exhaustive search in the full angular range of 360 degrees. Typically, the result of wafer orientation based on notch alone is limited in accuracy and requires additional step of "Fine Alignment," which is time consuming. In order to avoid long mechanical movements, some of the existing solutions require additional hardware such as extra sensors, or an additional camera which covers a large part of the wafer within its field of view or several cameras. All those exhibit added complexity and cost.

BRIEF SUMMARY OF THE INVENTION

One aspect of the present invention provides a method of estimating a position of a wafer notch, the method comprising capturing an image of one or more specified region(s) of the wafer, identifying a principle angle in a transformation of the captured image which is converted into polar coordinates, and recovering one or more wafer axis (or axes) from an identified principle angle.

These, additional, and/or other aspects and/or advantages of the present invention are set forth in the detailed description which follows; possibly inferable from the detailed description; and/or learnable by practice of the present invention.

BRIEF DESCRIPTION OF THE DRAWINGS

For a better understanding of embodiments of the invention and to show how the same may be carried into effect, reference will now be made, purely by way of example, to the accompanying drawings in which like numerals designate corresponding elements or sections throughout.

In the accompanying drawings:

FIG. 5 is a high level schematic flowchart of a method, according to some embodiments of the invention.

DETAILED DESCRIPTION OF THE INVENTION

Figure 1:
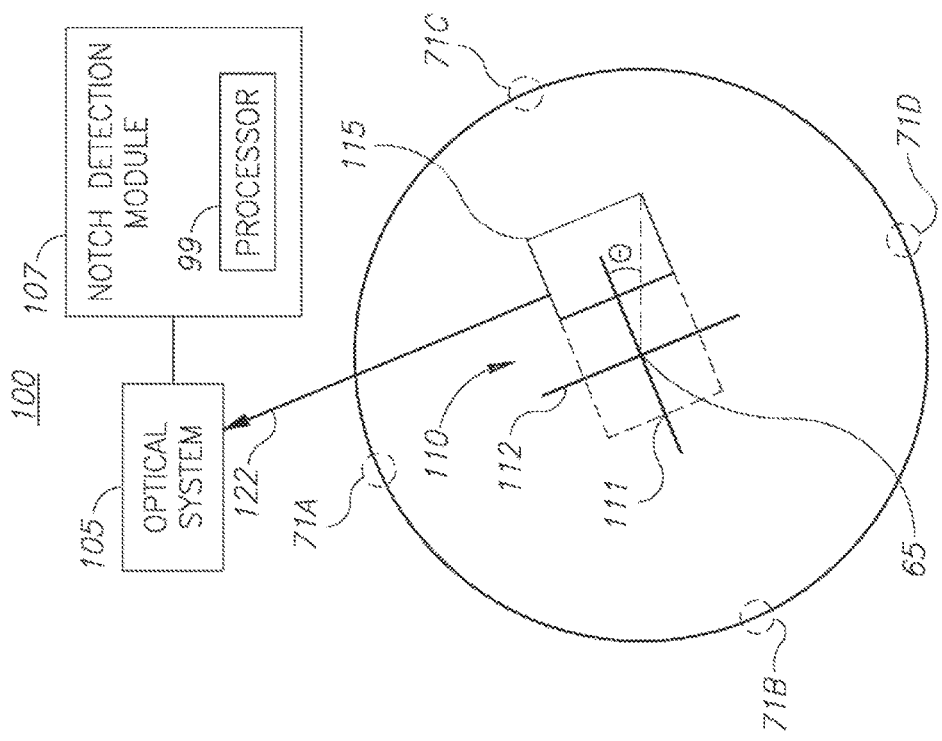
FIG. 1 is a high level schematic illustration of a wafer with its notch and a notch detection module associated with an optical system within a metrology system, according to some embodiments of the invention.
Figure 1:
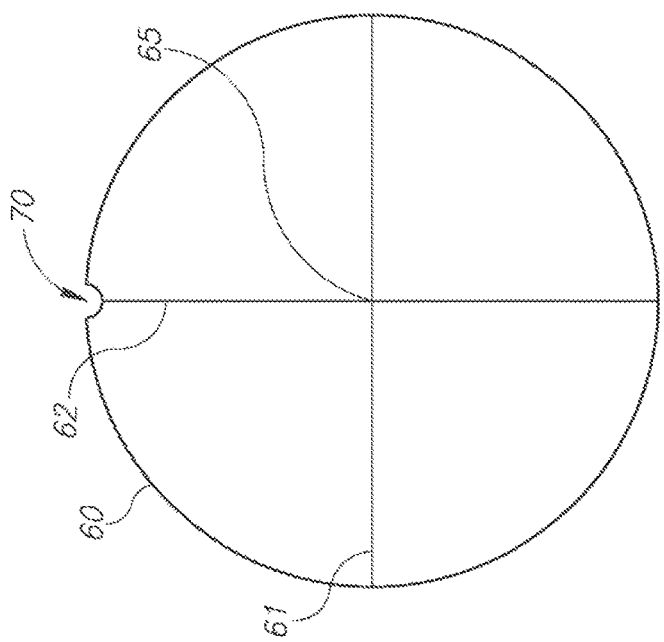

Prior to the detailed description being set forth, it may be helpful to set forth definitions of certain terms that will be used hereinafter.

The term "geometric primitives" in an image, as used in this application refers to basic forms, objects and patterns in the image, such as lines, simple shapes or recurring elements.

The term "street orientation" as used in this application refers to orientations of geometric primitives in the image, e.g., with respect to a given grid. The term "street orientation algorithm" as used in this application refers to ways of deriving the street orientation.

It is further noted, that there is a strong geometrical correlation between one wafer axis and the other wafer axes, and respectively between the principle angle to one wafer axis and the principle angles to the other wafer axes. Geometrically, the wafer axes are separated by multiples of 90° as are the principle angles with respect to the wafer axes. Hence, in the following description, any aspect relating to one wafer axis and/or one principle angle is to be understood as potentially relating to any number of wafer axes and/or principle angles. For example, any orientation measurement may be carried out with respect to one or more wafer axes.

With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how the several forms of the invention may be embodied in practice.

Before at least one embodiment of the invention is explained in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Notch detection methods and modules are provided for efficiently estimating a position of a wafer notch. Capturing an image of specified region(s) of the wafer, a principle angle is identified in a transformation, converted into polar coordinates, of the captured image. Then the wafer axes are recovered from the identified principle angle as the dominant orientations of geometric primitives in the captured region. The captured region may be selected to include the center of the wafer and/or certain patterns that enhance the identification and recovering of the axes. Multiple images and/or regions may be used to optimize image quality and detection efficiency. The angular orientation of the wafer is measured with high accuracy in minimal time, by simultaneous minimization of algorithmic complexity and mechanical movements of the vision system with respect to the wafer. The notch position may be detected implicitly, without directly sensing it. Certain embodiments overcome the challenges produced by the tool architecture such as: limited field of view of the vision system and the time-consuming mechanical movements for positioning of the camera with respect to the wafer both lateral and rotational, as well as image corruption by various types of noise.

It is assumed that the orientation of the wafer at the beginning of the procedure is arbitrary and that the wafer deviation from the chuck center is limited to a 2 mm error. The computation of wafer orientation may be triggered in the system as part of either "Train" or "Run" sequences. The time optimization of the "Run" sequence is the most critical because it directly affects the throughput of the tool. Disclosed modules and methods use a Street Orientation Algorithm to reduce the search space of orientation and notch position to four points, for example, a robust algorithm for Street Orientation may be used to enable skipping the fine alignment step. In addition, anchor points may be used to avoid long mechanic movements from center of wafer, as described below.

FIG. 1 is a high level schematic illustration of a wafer 60 with its notch 70 and a notch detection module 107 associated with an optical system 105 within a metrology system 100, according to some embodiments of the invention. It is noted that disclosed methods and modules may be applied to systems in the semiconductor industry other than metrology systems and that the latter merely serve in the present disclosure as a non-limiting example.

The orientation of wafer 60 is uniquely defined by the position of its notch 70. The periodic layout of devices printed on wafer 60 and the borders of dies are aligned along the Cartesian axes 61, 62, with notch 70 is at the end-point of y axis 62.

Instead of detecting notch 70 visually at the periphery of wafer 60, e.g., by imaging whole wafer 60 with respective axes 61, 62 and center 65, or imaging the wafer periphery, notch detection module 107 merely images 110 a central region 115 of wafer 60, which may include wafer center 65 or not, and derives from the imaged region the orientations 111, 112 of wafer axes 61, 62. For example, central region 115 may comprise unique pattern(s) with known position with respect to center of wafer 65. Notch detection module 107 uses derived orientations 111, 112 to suggest possible locations 71A-71D for notch 70, and in certain embodiments also proceeds to determine which of locations 71A-71D is the actual notch location. Image(s) 110 of central region(s) 115 may be selected from multiple image(s) 110 and/or multiple regions 115, e.g., according to image quality, derivation quality, or derivations from multiple image(s) 110 and/or multiple regions 115 may be statistically analyzed to derive more accurate location estimations.

Notch detection module 107 may implement any of the following components of the orientation computation task:
i. A "street orientation algorithm" may be used to find the dominant orientation (designated by the angle θ) of geometric primitives in the field of view (FOV) of imaging device 100, for example with respect to image 110 acquired at an estimated center of wafer 60.

ii. A "notch detection algorithm" may comprise searching specified notch pattern(s) in up to three (out of four) possible locations 71A-71D at the edge of wafer 60 according to detected orientations 111, 112.

iii. An "anchor point training algorithm" may comprise searching and defining the unique pattern(s) for selection of region 115, e.g., in the near proximity to center 65 of wafer 60.

iv. An "anchor point detection algorithm" may comprise pattern searching of anchor point template(s) near center 65 of wafer 60 as basis for the anchor point training algorithm.

It is noted that the estimation of street orientation and hence of the orientation of the wafer axes may be carried out by itself. Additionally, estimation of the notch location and/or usage of anchor points or patterns as proxies for the notch location may be applied to derive the notch location from the street orientation without applying direct imaging of the notch region.

Figure 2:
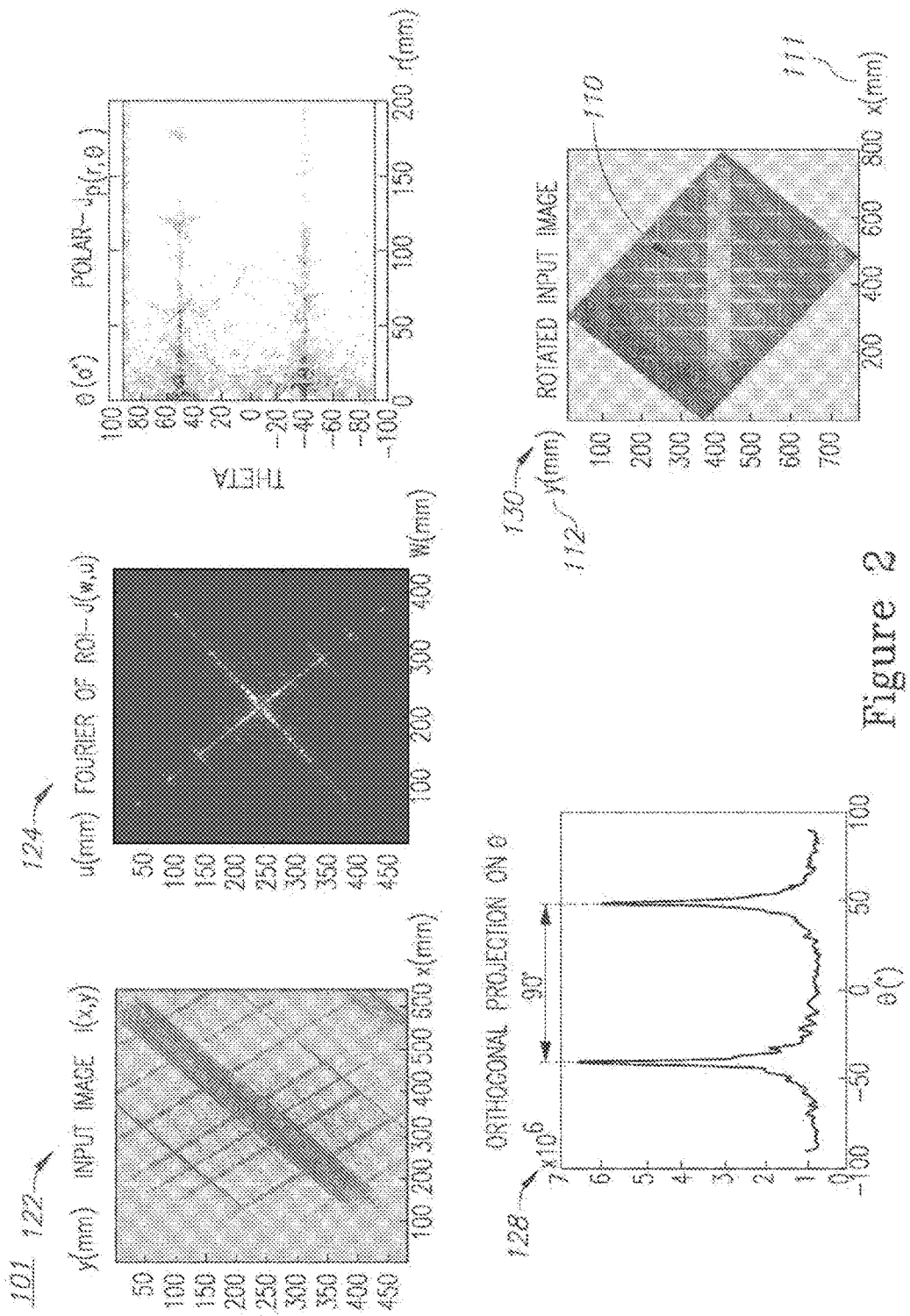
FIG. 2 is a high level schematic illustration of intermediate steps in a street orientation algorithm, operable by the notch detection module, according to some embodiments of the invention.

FIG. 2 is a high level schematic illustration of intermediate steps in a street orientation algorithm 101, operable by notch detection module 107, according to some embodiments of the invention. In certain embodiments, street orientation algorithm 101 relies on image analysis in the Fourier domain. Unlike other edge-based approaches the inventors found this method to be extremely fast and robust to noisy, out-of-focus and low-contrast inputs (images 110). The steps of proposed algorithm 101 are illustrated in FIG. 2.

Upon captured image 122, shown in schematic wafer coordinates and designated $I(x,y)$, the 2D (two dimensional) Discrete Fourier Transform is applied and the absolute value of the Fourier coefficients are computed and presented as an image 124, denoted $J(w,u)$. Then, $J(w,u)$ is converted to polar coordinates to yield $J_P(r,\theta)$ (illustrated in image 126) and the orthogonal projection thereof onto the θ axis 128 is used for the orientation recovery using the resulting peaks separated by 90°, giving θ and θ+90°. Deriving θ, rotated image 130 may be generated from captured image 122, with rotated image 130 characterized by orientations 111, 112 that are congruent to wafer axes 61, 62. Notch 70 is located at one of the ends of one of orientations 111, 112. In certain embodiments, an ambiguity in the relative angle between orientations 111, 112 and wafer axes 61, 62 (among θ 71A, θ+90° 71C, θ+180° 71D and θ+270° 71B) may be resolved via notch pattern search (in "Train" sequences) or anchor pattern search (in "Run" sequences), both possibly implemented as multi-scale rigid template matching with known scale and orientation.

The inventors have performed an accuracy and time requirements analysis, exemplified in the following by a few experimental results which demonstrate the robustness of proposed street orientation approach 101 to eliminate the need for any additional fine alignment step.

Figure 3:
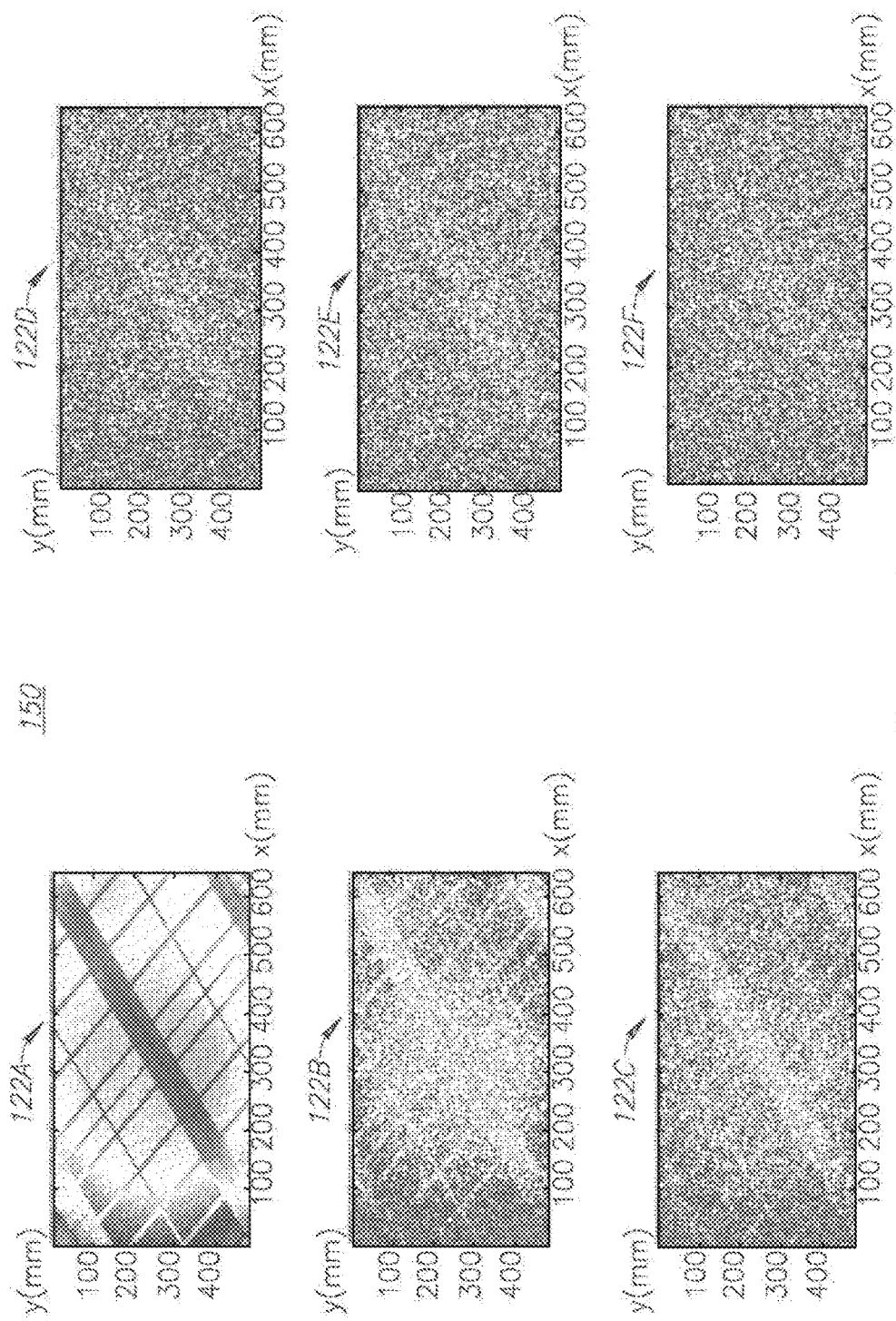
FIG. 3 is an illustration of exemplary inputs onto which the street orientation algorithm may be applied, displaying increasing levels of noise, according to some embodiments of the invention.

FIG. 3 is an illustration of exemplary inputs 150 onto which street orientation algorithm 101 may be applied, displaying increasing levels of noise, according to some embodiments of the invention. Street orientation algorithm 101 is applied on input image 122 with synthetically added noise of varying level (single run) to yield images 122A-122F with increasing levels of noise (the black and white illustrations miss some of the color coded information, especially in images 122C, 122D). The mean and the standard deviation of the intensities of input images 122 are standardized to be between 0 and 1 with noise standard deviation ranging from 0 (122A, resulting in accurate θ=−40.481° for the specifically illustrated example) through 1 (122B, θ=−40.486°), 2 (122C, θ=−40.471°) and 4 to 6

(122D-F and θ=−40.486°, θ=−40.504° and θ=−45.000° respectively). The inventors thus observed that even under very heavy added white noise with standard deviation 5 (122E), the error in θ resulting from street orientation algorithm 101 and/or notch detection module 107 is much smaller than 0.25°, which practically eliminates the need of fine alignment in system 100 under many circumstances.

Figure 4:
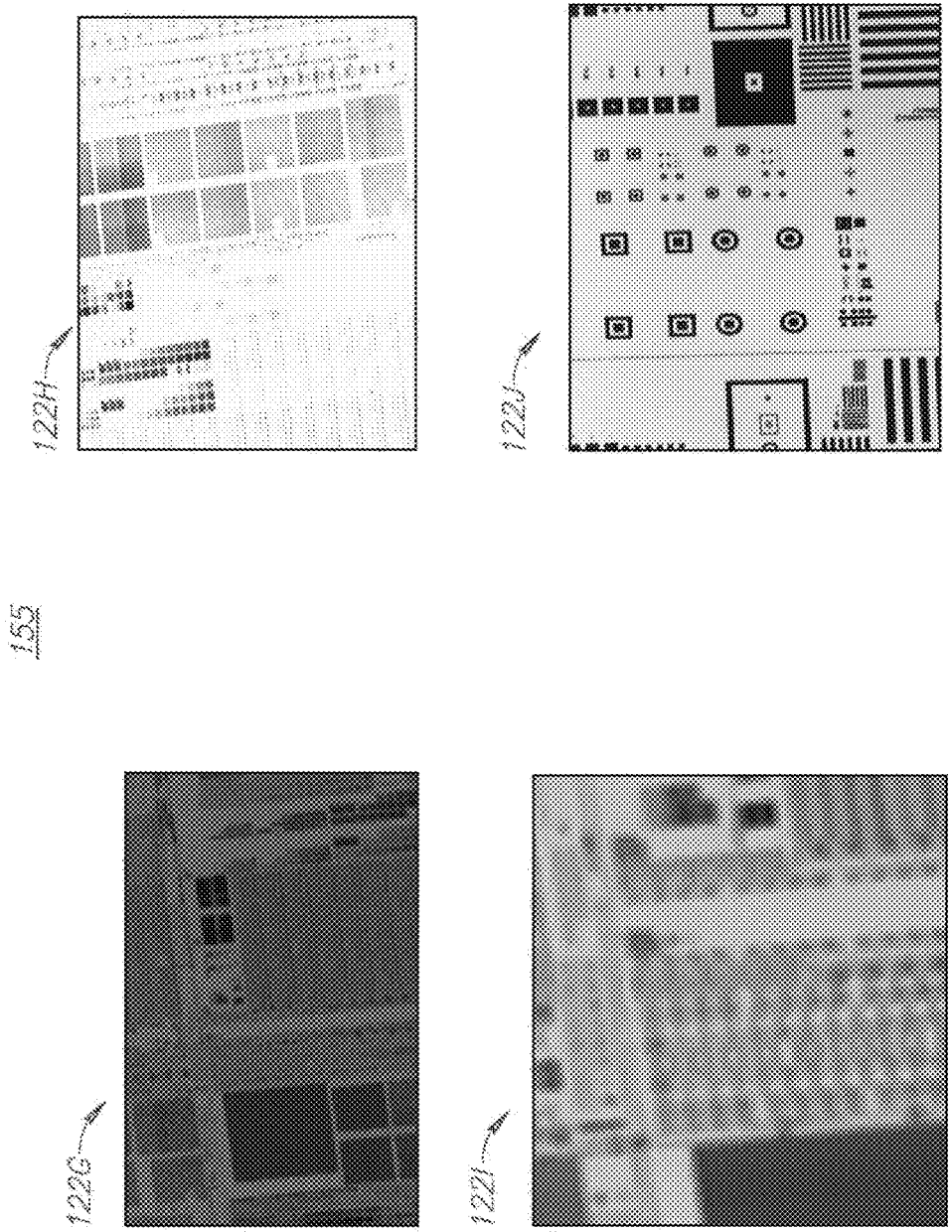
FIG. 4 is an illustration of exemplary input images from different wafer regions for selection according to their characteristics, according to some embodiments of the invention.

FIG. 4 is an illustration of exemplary input images 155 from different wafer regions 115, for selection of image 122 according to their characteristics, according to some embodiments of the invention. It is noted that different wafer regions 115 may comprise different regions on one wafer 60 or on different wafers 60.

In certain embodiments, multiple images 122G-J may be captured from different regions 115 on wafer and one or more images 122 may be selected therefrom by notch detection module 107 for applying the notch detection analysis such as street orientation algorithm 101. In illustrated non-limiting example 155, input images 122G-J may be acquired on wafer 60 with arbitrary orientations at a specified number of different locations. Since no additional rotation of wafer 60 is applied between acquisitions the orientation result (θ and/or notch position) is expected to be the same so that the results from multiple images 122 may be compared and analyzed, e.g., statistically by measuring scattering metrics of the results. Experiments may be repeated for several wafers 60, at various orientations, various imaging conditions (contrast and focus) to optimize the selection of region(s) 115. In addition, comparing edge-based algorithm (EB) to Fourier Transform-based algorithms (FTB) 101 illustrates the superiority of the latter.

In 29 images 122 taken from different wafers 60 and/or different regions 115, and with respect to accuracy metrics of range (of measured angles θ)>0.3° and standard deviation (of measured angles θ)>0.2°, all FTB measurements conformed with both metrics, while in 11 and 9 EB measurements the metric's threshold were exceeded (respectively). FIG. 4 illustrates as examples image 122G suffering from insufficient illumination and low contrast (in FTB $\theta_{range}$=0.050 $\theta_{STD}$=0.018 while in EB $\theta_{range}$=0.200 $\theta_{STD}$=0.057), image 122H suffering from saturation and low contrast (in FTB $\theta_{range}$=0.112 $\theta_{STD}$=0.032 while in EB $\theta_{range}$=0.400 $\theta_{STD}$=0.119), image 122I being out of focus (in FTB $\theta_{range}$=0.031 $\theta_{STD}$=0.032 while in EB $\theta_{range}$=0.780 $\theta_{STD}$=0.266) and image 122J exhibiting atypical wafer design (in FTB $\theta_{range}$=0.105 $\theta_{STD}$=0.032 while in EB $\theta_{range}$=0.390 $\theta_{STD}$=0.168), all exhibiting the better performance of the disclosed invention. It is noted that the results of street orientation algorithm 101 were stable even for out-of-focus and low-contrast inputs 122 and way below the limits which require additional refinement steps. It is further noted that while from a theoretical point of view, the most time-consuming operator is the Fourier Transform (O(N log N)), where N is the number of pixels in input image 122, yet in practice, the computation time is negligible with comparison to the time required for the mechanical movement of the camera in optical system 100 with respect to wafer 60.

FIG. 5 is a high level schematic flowchart of a method 200, according to some embodiments of the invention. Method 200 comprises estimating a position of a wafer notch (stage 210) and may be at least partially carried out by at least one computer processor 99 (stage 280).

Method 200 may comprise capturing an image of a specified region of the wafer (stage 220), e.g., capturing an image of a central region of the wafer (stage 222), and possibly capturing multiple images and selecting images for further processing according to image characteristics (stage 225). Method 200 may employ any algorithm for finding the dominant orientation (designated by the angle θ) of geometric primitives in the field of view (FOV) of imaging device 100, for example with respect to image 110 acquired at an estimated center of wafer 60 (stage 228).

Method 200 may further comprise transforming the captured image (stage 230), calculating Fourier transform coefficients for the captured image (stage 235), converting the transformed image into polar coordinates (stage 240) and projecting the converted transformed image orthogonally (stage 245), and may further comprise identifying principle angle(s) in the transformation of the captured image which is converted into polar coordinates (stage 250).

In certain embodiments, method 200 comprises recovering wafer axis(es) from the identified principle angle(s) (stage 260) and identifying the wafer notch from the recovered wafer axis(es) (stage 270), for example by searching specified notch pattern(s) along the recovered wafer axis(es) (stage 272), by searching and defining unique pattern(s) to be captured in the image, which allow notch identification (stage 274) and respective selection of the captured region, e.g., in the near proximity to the center of the wafer and/or by pattern searching of anchor point template(s) that indicate the axis along which the notch is located (stage 276).

Advantageously using street orientation 101 to calculate wafer orientation narrows down the search space of orientations to four possibilities and the quality of street orientation 101 exemplified above eliminates the need for extra time required for a fine alignment step. Consecutively, using anchor points allows performing short mechanical movement to identify the quadrate, i.e., and respectively the axis along which the notch is located. For example, an anchor point close to the center of wafer may be selected to allow little or no travelling of the optical head, which is advantageous with respect to prior art movement to the location of the notch at the edge of wafer. Method 200 thus requires short stroke movements and hence shorter operation time.

In the above description, an embodiment is an example or implementation of the invention. The various appearances of "one embodiment", "an embodiment", "certain embodiments" or "some embodiments" do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Certain embodiments of the invention may include features from different embodiments disclosed above, and certain embodiments may incorporate elements from other embodiments disclosed above. The disclosure of elements of the invention in the context of a specific embodiment is not to be taken as limiting their used in the specific embodiment alone.

Furthermore, it is to be understood that the invention can be carried out or practiced in various ways and that the invention can be implemented in certain embodiments other than the ones outlined in the description above.

The invention is not limited to those diagrams or to the corresponding descriptions. For example, flow need not move through each illustrated box or state, or in exactly the same order as illustrated and described.

Meanings of technical and scientific terms used herein are to be commonly understood as by one of ordinary skill in the art to which the invention belongs, unless otherwise defined.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A method of wafer notch detection comprising:
capturing an image, with an imaging device, of at least one specified region of the wafer;
performing, with one or more processors, a street orientation procedure comprising:
performing a transformation of the image;
converting the transformation of the image into polar coordinates; and
determining a plurality of candidate locations of the notch based on an orientation of geometric primitives in the field-of-view of the imaging device; and
identifying, with one or more processors, a location of the notch by performing one or more notch pattern searches on at least a portion of the plurality candidate locations.

2. The method of claim 1, wherein the determining a plurality of candidate locations of the notch based on an orientation of geometric primitives in the field-of-view of the imaging device comprises: determining a plurality of candidate locations of the notch based on a dominant orientation of geometric primitives in the field-of-view of the imaging device.

3. The method of claim 1, wherein the specified region of the wafer includes a center of the wafer.

4. The method of claim 1, wherein the transformation is a two dimensional Discrete Fourier Transform.

5. The method of claim 1, further comprising:
performing, with one or more processors, an anchor point detection procedure.

6. The method of claim 1, wherein the identifying, with one or more processors, a location of the notch by performing one or more notch pattern searches on at least a portion of the plurality candidate locations comprises searching at least one specified notch pattern along at least one derived wafer orientation.

7. The method of claim 1, further comprising:
performing, with one or more processors, an anchor point training procedure, wherein the anchor point training procedure includes searching and defining at least one unique pattern to be captured in the image, to facilitate notch identification.

8. The method of claim 1, further comprising:
capturing a plurality of images; and
selecting therefrom images for further processing according to image characteristics.

9. A system for wafer notch detection comprising:
an optical system, wherein the optical system is configured to capture an image of at least one selected region of a wafer, and
a computer processor configured to:
receive, from the optical system, the image of at least one specified region of a wafer;
perform a street orientation procedure comprising: performing a transformation of the image; converting the transformation of the image into polar coordinates; and determining a plurality of candidate locations of the notch based on an orientation of geometric primitives in the field-of-view of the imaging device,
wherein the computer processor is further configured to:
identify a location of the notch by performing one or more notch pattern searches on at least a portion of the plurality candidate locations.

10. The system for notch detection of claim 9, wherein the transformation is a two dimensional Discrete Fourier Transform.

11. The system for notch detection of claim 9, wherein the computer processor is further configured to performing an anchor point detection procedure.

12. The system for notch detection of claim 11, wherein the computer processor is further configured to identify a location of the notch by performing one or more notch pattern searches on at least a portion of the plurality candidate locations by searching at least one specified notch pattern along at least one derived wafer orientation.

13. The system for notch detection of claim 9, wherein the computer process is further configured to perform an anchor point training procedure, wherein the anchor point training procedure includes searching and defining at least one unique pattern to be captured in the image, to facilitate notch identification.

14. The system for notch detection of claim 9, wherein the optical system is configured to capture a plurality of images, wherein the computer processor is configured to select from the plurality of images a set of images for further processing according to one or more image characteristics.

15. The method of claim 3, wherein the center of the wafer contains one or more patterned structures, wherein the patterned structures are aligned with one or more axes of the wafer.

16. The method of claim 8, wherein the plurality of images are captured from different portions of the wafer.

17. The method of claim 1, wherein the imaging device comprises a camera within a metrology system.

18. The system of claim 9, wherein the center of the wafer contains one or more patterned structures, wherein the patterned structures are aligned with one or more axes of the wafer.

19. The system of claim 14, wherein the plurality of images are captured from different portions of the wafer.

20. The system of claim 9, wherein the optical system comprises an optical system within a metrology system.

* * * * *